United States Patent
Morisset (10) Patent No.: US 10,231,950 B2
(45) Date of Patent: *Mar. 19, 2019

(54) ERYTHROMELALGIA TREATMENT

(71) Applicant: Convergence Pharmaceuticals Limited, London (GB)

(72) Inventor: Valerie Morisset, Cambridge (GB)

(73) Assignee: Convergence Pharmaceuticals Limited, Maidenhead (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/516,031

(22) PCT Filed: Oct. 2, 2015

(86) PCT No.: PCT/GB2015/052885
§ 371 (c)(1),
(2) Date: Mar. 31, 2017

(87) PCT Pub. No.: WO2016/051194
PCT Pub. Date: Apr. 7, 2016

(65) Prior Publication Data
US 2017/0304264 A1    Oct. 26, 2017

(30) Foreign Application Priority Data
Oct. 3, 2014 (GB) .................................. 1417497.3

(51) Int. Cl.
*A61K 31/401* (2006.01)
*C07D 207/04* (2006.01)
*C12Q 1/6883* (2018.01)

(52) U.S. Cl.
CPC .......... *A61K 31/401* (2013.01); *C07D 207/04* (2013.01); *C12Q 1/6883* (2013.01); *C12Q 2600/106* (2013.01); *C12Q 2600/156* (2013.01)

(58) Field of Classification Search
CPC .......................... A61K 31/401; C07D 207/04
See application file for complete search history.

(56) References Cited

U.S. PATENT DOCUMENTS 8,093,268 B2 * 1/2012 Alvaro ................. A61K 31/401
514/326
9,493,449 B2 * 11/2016 Yao ....................... C07D 403/12
2017/0096708 A1 * 4/2017 Morisset ............... C12Q 1/6883

OTHER PUBLICATIONS

Bagal, S. K., et al.: "Recent progress in sodium channel modulators for pain", Bioorganic & Medicinal Chemistry Letters, vol. 24, No. 16, Jun. 21, 2014 (Jun. 21, 2014), pp. 3690-3699, XP029041706, ISSN: 0960-894X.

Goldberg, Y. P., et al.: "Human Mendelian pain disorders: a key to discovery and validation of novel analgesics", Clinical Genetics, vol. 82, No. 4, Aug. 13, 2012 (Aug. 13, 2012), pp. 367-373, XP055235037, DK. ISSN: 0009-9163.

Tate, S., et al.: "CNV1014802 a novel potent state-dependent sodium channel blocker with broad preclinical antihyperalgesic efficacy", Abstracts of the Annual Meeting of the Society for Neuroscience, Society for Neuroscience, Washington, DC, US, No. 41, Nov. 12, 2011 (Nov. 12, 2011), pp. 1-4, XP008178393, ISSN: 0190-5295.

* cited by examiner

*Primary Examiner* — Sun Jae Yoo
(74) *Attorney, Agent, or Firm* — Foley Hoag LLP; David P. Halstead; Lucas P. Watkins (57) ABSTRACT

The present invention is directed to the treatment of erythromelalgia comprising administering to a subject in need thereof, a therapeutically effective amount of 5-(4-{[(2-fluorophenyl)methyl]oxy}phenyl)-prolinamide or a pharmaceutically acceptable salt, solvate or prodrug thereof.

9 Claims, 2 Drawing Sheets

FIG. 1

FIG.1 (ctd)

ERYTHROMELALGIA TREATMENT

CROSS-REFERENCE TO RELATED APPLICATIONS

This application is a 35 U.S.C. § 371 United States National Phase Application of, and claims priority to, PCT Application No. PCT/GB2015/052885, filed Oct. 2, 2015, which claims priority to Great Britain Application No. 1417497.3, filed Oct. 3, 2014. The entire contents of the aforementioned applications are incorporated herein.

FIELD OF THE INVENTION

The present invention is directed to the treatment of erythromelalgia comprising administering to a subject in need thereof, a therapeutically effective amount of 5-(4-{[(2-fluorophenyl)methyl]oxy}phenyl)-prolinamide or a pharmaceutically acceptable salt, solvate or prodrug thereof.

BACKGROUND

Erythromelalgia is a disorder that typically affects the skin of the feet or hands, or both, and causes visible redness, intense heat and severe pain. In many cases the use of measures, such as the avoidance of warm temperatures or ongoing elevation required by some with severe erythromelalgia, mean that patients often have to make major adjustments to their lifestyles to avoid flare-ups. The cause of erythromelalgia is unknown in the vast majority of cases, and although a number of medications have been used to help relieve symptoms, there is no single cure available. Erythromelalgia is a rare disease and approximately 15% of erythromelalgia cases have been associated with Nav1.7 gain of function mutations (Dib-Hajj et al (2013) Nature Reviews Neuroscience 14, 49-62; www.ghr.nlm.nih.gov/condition/erythromelalgia).

Thus, there is a need to provide an effective treatment for erythromelalgia to help patients treat their symptoms.

WO 2007/042239 describes 5-(4-{[(2-fluorophenyl)methyl]oxy}phenyl)-prolinamide having the following formula:

and pharmaceutically acceptable salts, solvates or prodrugs thereof.

Themistocleous et al. (2014) *Pract. Neurol.* 0:1-12 describes that gain of function mutations in $Na_v1.7$ are believed to cause erythromelalgia and paroxysmal extreme pain disorder.

DETAILED DESCRIPTION OF THE INVENTION

According to a first aspect of the invention, there is provided (5R)-5-(4-{[(2-fluorophenyl)methyl]oxy}phenyl)-L-prolinamide or a pharmaceutically acceptable salt, solvate or prodrug thereof for use in the treatment of erythromelalgia.

According to a further aspect of the invention, there is provided a method for the treatment of erythromelalgia comprising administering to a subject in need thereof, a therapeutically effective amount of (5R)-5-(4-{[(2-fluorophenyl)methyl]oxy}phenyl)-L-prolinamide or a pharmaceutically acceptable salt, solvate or prodrug thereof.

The invention also provides the use of (5R)-5-(4-{[(2-fluorophenyl)methyl]oxy}phenyl)-L-prolinamide, or a pharmaceutically acceptable salt, solvate or prodrug thereof, in the manufacture of a medicament for the treatment of erythromelalgia.

In one embodiment, the subject to be treated is a human.

A reference to (5R)-5-(4-{[(2-fluorophenyl)methyl]oxy}phenyl)-L-prolinamide also includes ionic forms, salts, solvates, isomers (including geometric and stereochemical isomers), tautomers, N-oxides, esters, prodrugs, isotopes and protected forms thereof; preferably, the salts or tautomers or isomers or N-oxides or solvates thereof; and more preferably, the salts or tautomers or N-oxides or solvates thereof, even more preferably the salts or tautomers or solvates thereof.

(5R)-5-(4-{[(2-Fluorophenyl)methyl]oxy}phenyl)-L-prolinamide can exist in the form of a salt, for example an acid addition salt or, in certain cases a salt of organic and inorganic bases such as a carboxylate, sulfonate and phosphate salt. All such salts are within the scope of this invention, and references to (5R)-5-(4-{[(2-fluorophenyl)methyl]oxy}phenyl)-L-prolinamide include the salt forms of this compound.

The pharmaceutically acceptable salts of (5R)-5-(4-{[(2-fluorophenyl)methyl]oxy}phenyl)-L-prolinamide are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, *J. Pharm, Sci.*, 66, 1-19, 1977; P L Gould, *Int. J. Pharma.*, 33 (1986), 201-217; and Bighley et al, Encyclopedia of Pharmaceutical Technology, Marcel Dekker Inc, New York 1996, Volume 13, page 453-497.

The salts described herein can be synthesized from the parent compound that contains a basic or acidic moiety by conventional chemical methods such as methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

The compounds of the invention may exist as mono- or di-salts depending upon the $pK_a$ of the acid from which the salt is formed.

It will be appreciated that for use in medicine the salts of the compounds should be pharmaceutically acceptable. Suitable pharmaceutically acceptable salts will be apparent to those skilled in the art. Pharmaceutically acceptable salts include those described by Berge, Bighley and Monkhouse, *J. Pharm. Sci.* (1977) 66, pp. 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds described herein, and are included within the scope of this invention. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In one embodiment, the (5R)-5-(4-{[(2-fluorophenyl)methyl]oxy}phenyl)-L-prolinamide or a pharmaceutically acceptable salt, solvate or prodrug thereof is selected from (5R)-5-(4-{[(2-fluorophenyl)methyl]oxy}phenyl)-L-prolinamide hydrochloride or (5R)-5-(4-{[(2-fluorophenyl)methyl]oxy}phenyl)-L-prolinamide methanesulfonate. In a further embodiment, the (5R)-5-(4-{[(2-fluorophenyl)methyl]oxy}phenyl)-L-prolinamide or a pharmaceutically acceptable salt, solvate or prodrug thereof is (5R)-5-(4-{[(2-fluorophenyl)methyl]oxy}phenyl)-L-prolinamide hydrochloride.

Certain of the compounds described herein may form acid addition salts with one or more equivalents of the acid. The present invention includes within its scope all possible stoichiometric and non-stoichiometric forms.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof.

It will be appreciated by those skilled in the art that certain protected derivatives of (5R)-5-(4-{[(2-fluorophenyl)methyl]oxy}phenyl)-L-prolinamide, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of suitable pro-drugs for the compounds of the present invention are described in *Drugs of Today*, Volume 19, Number 9, 1983, pp 499-538 and in *Topics in Chemistry*, Chapter 31, pp 306-316 and in "*Design of Prodrugs*" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "*Design of Prodrugs*" (the disclosure in which document is incorporated herein by reference) may be placed on appropriate functionalities when such functionalities are present within compounds of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

As used herein, unless otherwise noted, the term "erythromelalgia" (also known as Gerhardt disease, Mitchell disease or Weir-Mitchell disease) shall mean any disorder in which the blood vessels of a subject (preferably a human adult, child or infant) become inflamed and receive increased blood flow, causing visible redness, intense heat and burning pain, usually in the upper or lower extremities (i.e. hands and/or feet).

Erythromelalgia may be primary erythromelalgia (i.e. a disorder in itself) or secondary erythromelalgia (i.e. a symptom of another condition). Primary erythromelalgia is an autosomal dominant disorder thought to be caused by a mutation in the $Na_v1.7$ sodium ion channel gene, SCN9A. Secondary erythromelalgia may result as a symptom of another disorder, such as bone marrow disorders (e.g. myeloproliferative disorders), neuropathies, certain autoimmune connective tissue diseases, or result from the administration of certain drugs (e.g. bromocriptine, nifedipine, nicardipine), or mushroom or mercury poisoning.

In one embodiment, the disorder is selected from primary erythromelalgia or secondary erythromelalgia. In a further embodiment, the disorder is primary erythromelalgia. In an alternative embodiment, the disorder is secondary erythromelalgia.

The term "subject" as used herein, refers to an animal, preferably a mammal, most preferably a human adult, child or infant, who has been the object of treatment, observation or experiment.

It will be appreciated that references herein to "treatment" extend to prophylaxis, prevention of recurrence and suppression or amelioration of symptoms (whether mild, moderate or severe) as well as the treatment of established conditions.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the symptoms of the disease or disorder being treated; and/or reduction of the severity of one or more of the symptoms of the disease or disorder being treated.

(5R)-5-(4-{[(2-Fluorophenyl)methyl]oxy}phenyl)-L-prolinamide or a pharmaceutically acceptable salt, solvate or prodrug thereof may also be used in combination with other therapeutic agents. The invention thus provides, in a further aspect, a combination comprising (5R)-5-(4-{[(2-fluorophenyl)methyl]oxy}phenyl)-L-prolinamide or a pharmaceutically acceptable salt, solvate or prodrug thereof together with a further therapeutic agent for use in the treatment of erythromelalgia.

(5R)-5-(4-{[(2-Fluorophenyl)methyl]oxy}phenyl)-L-prolinamide or a pharmaceutically acceptable salt, solvate or prodrug thereof may be used in combination with other medicaments indicated to be useful in the treatment or prophylaxis of pain (i.e. analgesics). Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO 99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the α2δ-subunit of voltage gated calcium channels, such as gabapentin, pregabalin and solzira; tricyclic antidepressants such as amitriptyline; neurone stabilising antiepileptic drugs; cholinesterase inhibitors such as galantamine; monoaminergic uptake inhibitors such as venlafaxine; opioid analgesics; local anaesthetics; 5HT1 agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at P2X3, P2X2/3, P2X4, P2X7 or P2X4/7; KCNQ/Kv7 channel openers, such as retigabine; additional COX-2 inhibitors as disclosed in U.S. Pat. No. 5,474,995, U.S. Pat. No. 5,633,272, U.S. Pat. No. 5,466,823, U.S. Pat. No. 6,310,099 and U.S. Pat. No. 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

In one embodiment, the present invention is directed to co-therapy, adjunctive therapy or combination therapy, comprising administration of (5R)-5-(4-{[(2-fluorophenyl)methyl]oxy}phenyl)-L-prolinamide or a pharmaceutically acceptable salt, solvate or prodrug thereof and one or more analgesics (e.g. tramadol or amitriptyline), anticonvulsant drugs (e.g. gabapentin, neurontin or pregabalin (i.e. Lyrica)) or antidepressant drugs (e.g. duloxetine (i.e. Cymbalta) or venlafaxine).

In this embodiment, therapeutically effective amount shall mean that amount of the combination of agents taken together so that the combined effect elicits the desired biological or medicinal response. For example, the therapeutically effective amount of co-therapy comprising administration of (5R)-5-(4-{[(2-fluorophenyl)methyl]oxy}phenyl)-L-prolinamide or a pharmaceutically acceptable salt, solvate or prodrug thereof and at least one suitable analgesic, anticonvulsant or antidepressant drugs would be the amount of (5R)-5-(4-{[(2-fluorophenyl)methyl]oxy}phenyl)-L-prolinamide or a pharmaceutically acceptable salt, solvate or prodrug thereof and the amount of the suitable analgesic, anticonvulsant or antidepressant drugs that when taken together or sequentially have a combined effect that is therapeutically effective. Further, it will be recognized by one skilled in the art that in the case of co-therapy with a therapeutically effective amount, the amount of (5R)-5-(4-{[(2-fluorophenyl)methyl]oxy}phenyl)-L-prolinamide or a pharmaceutically acceptable salt, solvate or prodrug thereof and/or the amount of the suitable analgesic, anticonvulsant or antidepressant drugs individually may or may not be therapeutically effective.

As used herein, the terms "co-therapy", "adjunctive therapy" and "combination therapy" shall mean treatment of a subject in need thereof by administering one or more analgesic, anticonvulsant or antidepressant agent(s) and (5R)-5-(4-{[(2-fluorophenyl)methyl]oxy}phenyl)-L-prolinamide or a pharmaceutically acceptable salt, solvate or prodrug thereof, wherein (5R)-5-(4-{[(2-fluorophenyl)methyl]oxy}phenyl)-L-prolinamide or a pharmaceutically acceptable salt, solvate or prodrug thereof and the analgesic, anticonvulsant or antidepressant agent(s) are administered by any suitable means, simultaneously, sequentially, separately or in a single pharmaceutical formulation.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

Where (5R)-5-(4-{[(2-fluorophenyl)methyl]oxy}phenyl)-L-prolinamide or a pharmaceutically acceptable salt, solvate or prodrug thereof and the analgesic, anticonvulsant or antidepressant agent(s) are administered in separate dosage forms, the number of dosages administered per day for each compound may be the same or different. (5R)-5-(4-{[(2-Fluorophenyl)methyl]oxy}phenyl)-L-prolinamide or a pharmaceutically acceptable salt, solvate or prodrug thereof and the analgesic, anticonvulsant or antidepressant agent(s) may be administered via the same or different routes of administration. Examples of suitable methods of administration include, but are not limited to, oral, intravenous (iv), intramuscular (im), subcutaneous (sc), intranasal, transdermal, and rectal. Compounds may also be administered directly to the nervous system including, but not limited to, intracerebral, intraventricular, intracerebroventhcular, intrathecal, intracisternal, intraspinal and/or pen-spinal routes of administration by delivery via intracranial or intravertebral needles and/or catheters with or without pump devices. (5R)-5-(4-{[(2-Fluorophenyl)methyl]oxy}phenyl)-L-prolinamide or a pharmaceutically acceptable salt, solvate or prodrug thereof and the analgesic, anticonvulsant or antidepressant agent(s) may be administered according to simultaneous or alternating regimens, at the same or different times during the course of the therapy, concurrently in divided or single forms.

Advantageously, (5R)-5-(4-{[(2-fluorophenyl)methyl]oxy}phenyl)-L-prolinamide or a pharmaceutically acceptable salt, solvate or prodrug thereof may be administered in a single daily dose, or the total daily dosage may be administered in divided doses of two, three or four times daily.

The present invention provides methods of treating erythromelalgia comprising administering to a subject in need thereof, a therapeutically effective amount of (5R)-5-(4-{[(2-fluorophenyl)methyl]oxy}phenyl)-L-prolinamide or a pharmaceutically acceptable salt, solvate or prodrug thereof as described herein.

(5R)-5-(4-{[(2-Fluorophenyl)methyl]oxy}phenyl)-L-prolinamide or a pharmaceutically acceptable salt, solvate or prodrug thereof may be administered as the raw chemical but the active ingredient is preferably presented as a pharmaceutical composition.

As used herein, the term "composition" is intended to encompass a product comprising the specified ingredients in the specified amounts, as well as any product which results, directly or indirectly, from combinations of the specified ingredients in the specified amounts.

Since the compounds described herein are intended for use in pharmaceutical compositions it will readily be understood that they are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the pharmaceutical compositions.

According to a further aspect of the invention, there is provided a pharmaceutical composition comprising (5R)-5-(4-{[(2-fluorophenyl)methyl]oxy}phenyl)-L-prolinamide or a pharmaceutically acceptable salt, solvate or prodrug thereof for use in the treatment of erythromelalgia.

In one embodiment, the pharmaceutical composition comprises one or more pharmaceutically acceptable carrier(s), diluent(s) and/or excipient(s). The carrier, diluent and/or excipient must be "acceptable" in the sense of being compatible with the other ingredients of the composition and not deleterious to the recipient thereof.

Pharmaceutical compositions containing (5R)-5-(4-{[(2-fluorophenyl)methyl]oxy}phenyl)-L-prolinamide or a pharmaceutically acceptable salt, solvate or prodrug thereof as the active ingredient can be prepared by intimately mixing the compound with a pharmaceutical carrier according to conventional pharmaceutical compounding techniques. These procedures may involve mixing, granulating and compressing or dissolving the ingredients as appropriate to the desired preparation.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The compounds or their pharmaceutically acceptable salts may be administered by any convenient method, e.g. by oral, parenteral, buccal, sublingual, nasal, rectal or transdermal administration, and the pharmaceutical compositions adapted accordingly, for administration to mammals including humans.

The compounds or their pharmaceutically acceptable salts which are active when given orally can be formulated as liquids or solids, e.g. as syrups, suspensions, emulsions, tablets, capsules or lozenges.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non aqueous vehicles (which may include edible oils), for example almond oil, oily esters such as glycerine, propylene glycol, or ethyl alcohol; preservatives, for example methyl or propyl p hydroxybenzoate or sorbic acid, and, if desired, conventional flavouring or colouring agents.

Typical parenteral compositions consist of a solution or suspension of the active ingredient in a sterile vehicle, water being preferred, or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chloro-hydro-carbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin. Compositions for rectal administration are conveniently in the form of suppositories containing a conventional suppository base such as cocoa butter. Compositions suitable for transdermal administration include ointments, gels and patches.

In one embodiment the composition is in unit dose form such as a tablet, capsule or ampoule.

The dose of the compound or a pharmaceutically acceptable salt thereof, used in the treatment of the abovementioned disorders or diseases will vary in the usual way with the particular disorder or disease being treated, the weight of the subject and other similar factors. However, as a general rule, suitable unit doses may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be in the range of 50 mg to 1500 mg per day, for example 120 mg to 1000 mg per day. Such therapy may extend for a number of weeks or months.

It will be recognised by one of skill in the art that the optimal quantity and spacing of individual dosages of (5R)-5-(4-{[(2-fluorophenyl)methyl]oxy}phenyl)-L-prolinamide or a pharmaceutically acceptable salt, solvate or prodrug thereof will be determined by the nature and extent of the condition being treated, the form, route and site of administration, and the particular mammal being treated, and that such optimums can be determined by conventional techniques. In addition, factors associated with the particular patient being treated, including patient age, weight, diet and time of administration, will result in the need to adjust dosages. It will also be appreciated by one of skill in the art that the optimal course of treatment, i.e., the number of doses of a compound of the invention given per day for a defined number of days, can be ascertained by those skilled in the art using conventional course of treatment determination tests.

Diagnosis

According to a further aspect of the invention, there is provided a method of diagnosing erythromelalgia in a human subject wherein said method comprises detecting the presence of one or more genetic variations within the CACNA1A gene and/or the CACNA1B gene of said subject.

References herein to "CACNA1A gene" refer to the calcium channel, voltage-dependent, P/Q type, alpha 1A subunit gene (also known as Cav2.1). The CACNA1A gene belongs to a family of genes that code for the pore forming alpha subunits of calcium channels. These channels, which transport positively charged calcium atoms (calcium ions) across cell membranes, play a key role in a cell's ability to generate and transmit electrical signals. Calcium ions are involved in many different cellular functions, including cell-to-cell communication, the tensing of muscle fibers (muscle contraction), and the regulation of certain genes.

The CACNA1A gene provides instructions for making one part (the alpha-1 subunit) of a calcium channel called Cav2.1. This subunit forms the hole (pore) through which calcium ions can flow. Cav2.1 channels play an essential role in communication between nerve cells (neurons) in the brain and spinal cord. These channels help control the release of neurotransmitters, which are chemicals that relay signals from one neuron to another. It is believed that Cav2.1 channels are also involved in the survival of neurons and the ability of these cells to change and adapt over time (plasticity).

Near one end of the CACNA1A gene, a segment of three DNA building blocks (nucleotides) is repeated multiple times. This sequence, which is written as CAG, is called a triplet or trinucleotide repeat. In most people, the number of CAG repeats in this gene ranges from 4 to 18.

The CACNA1A gene is located on the short (p) arm of chromosome 19 at position 13 (19p13). More precisely, the molecular location of the CACNA1A gene is on chromosome 19: base pairs 13,206,441 to 13,506,459.

CACNA1A has been previously linked with episodic ataxia, familial hemiplegic migraine, spinocerebellar ataxia type 6 and sporadic hemiplegic migraine.

References herein to "CACNA1B gene" refer to the calcium channel, voltage-dependent, N type, alpha 1B subunit gene (also known as Cav2.2). The protein encoded by this gene is the pore-forming subunit of an N-type voltage-dependent calcium channel, which controls neurotransmitter release from neurons. The encoded protein forms a complex with alpha-2, beta, and delta subunits to form the high-voltage activated channel. This channel is sensitive to omega-conotoxin-GVIA and omega-agatoxin-IIIA but insensitive to dihydropyridines. Two transcript variants encoding different isoforms have been found for this gene.

The CACNA1B gene is located on the long (q) arm of chromosome 9 at position 34 (9q34). More precisely, the molecular location of the CACNA1B gene is on chromosome 9: base pairs 140,772,241 to 141,019,076.

Diseases associated with CACNA1B include krukenberg carcinoma, and morvan's fibrillary chorea, and among its related super-pathways are synaptic vesicle pathway and circadian entrainment.

References herein to "genetic variation" refer to a difference or variation between the genetic code or sequence of a human subject when compared with a wild-type or native genetic code or sequence. It will be appreciated that the genetic variations include any variation in the wild type or native genetic code of the genome from said human subject under analysis. Examples of such genetic variations include: mutations (e.g. point mutations), insertions, substitutions, deletions, frame shifts, single nucleotide polymorphisms (SNPs), haplotypes, chromosome abnormalities, copy number variation (CNV), epigenetics and DNA inversions. In one embodiment, the genetic variations are selected from substitutions, insertions, deletions and frame shifts.

References herein to the term "single-nucleotide polymorphism (SNP)" is intended to refer to DNA sequence variation occurring when a single nucleotide in the genome (or other shared sequence) differs between members of a species or between paired chromosomes in an individual.

References herein to the term "haplotype" is intended to refer to a set of genetic markers that are inherited together as a consequence of their chromosomal co-localization. Haplotype may refer to as few as two genetic variants or to an entire chromosome depending on the number of recombination events that have occurred between a given set of variants.

In one embodiment, the genetic variations are detected within the CACNA1A gene. In a further embodiment, the genetic variations are within the CACNA1A gene and are between 13,300,000 bp and 13,450,000 bp on chromosome 19, such as between 13,318,000 bp and 13,412,000 bp on chromosome 19.

The methods of the invention may be used to detect genetic variations using a biological sample obtained from the human subject. Thus, in one embodiment, the method initially comprises the step of obtaining a biological sample from the human subject.

The nucleic acid may be isolated from the sample according to any methods well known to those of skill in the art. Examples include tissue samples or any cell-containing or a cellular biomaterial (i.e. a bodily fluid or hair sample). Biological samples may be obtained by standard procedures and may be used immediately or stored, under conditions appropriate for the type of biological sample, for later use.

Methods of obtaining biological samples are well known to those of skill in the art and include, but are not limited to, aspirations, tissue sections, drawing of blood or other fluids, surgical or needle biopsies, and the like. Examples of suitable biological samples include: whole blood, blood serum, plasma, urine, saliva, or other bodily fluid (stool, tear fluid, synovial fluid, sputum), hair, cerebrospinal fluid (CSF), or an extract or purification therefrom, or dilution thereof. Biological samples also include tissue homogenates, tissue sections and biopsy specimens from a live subject. The samples can be prepared, for example where appropriate diluted or concentrated, and stored in the usual manner. In one embodiment, the biological sample is blood or serum. In a further embodiment, the biological sample is blood.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the cells of the human subject to detect using polymerase chain reaction.

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70° C. until thawed and used. "Fresh" plasma or serum should be refrigerated or maintained on ice until used, with nucleic acid (e.g., RNA, DNA or total nucleic acid) extraction being performed as soon as possible. Exemplary methods are described below.

Blood can be drawn by standard methods into a collection tube, typically siliconized glass, either without anticoagulant for preparation of serum, or with EDTA, sodium citrate, heparin, or similar anticoagulants for preparation of plasma. If preparing plasma or serum for storage, although not an absolute requirement, plasma or serum is first fractionated from whole blood prior to being frozen. This reduces the burden of extraneous intracellular RNA released from lysis of frozen and thawed cells which might reduce the sensitivity of the amplification assay or interfere with the amplification assay through release of inhibitors to PCR such as porphyrins and hematin. "Fresh" plasma or serum may be fractionated from whole blood by centrifugation, using gentle centrifugation at 300-800 times gravity for five to ten minutes, or fractionated by other standard methods. High centrifugation rates capable of fractionating out apoptotic bodies should be avoided.

It will be appreciated that the step of detecting the one or more genetic variations within the regions defined herein will comprise any suitable technique for genetic analysis.

The volume of plasma or serum used in the extraction may vary, but volumes of 1 to 100 ml of plasma or serum are usually sufficient.

Various methods of extraction are suitable for isolating the nucleic acid. Suitable methods include phenol and chloroform extraction. See Maniatis et al., Molecular Cloning, A Laboratory Manual, 2d, Cold Spring Harbor Laboratory Press, page 16.54 (1989).

Numerous commercial kits also yield suitable DNA and RNA including, but not limited to, QIAamp™ mini blood kit, Agencourt Genfind™, Roche Cobas® Roche MagNA Pure® or phenol: chloroform extraction using Eppendorf Phase Lock Gels®, and the NucliSens extraction kit (Biomerieux, Marcy l'Etoile, France). In other methods, mRNA may be extracted from blood/bone marrow samples using MagNA Pure LC mRNA HS kit and Mag NA Pure LC Instrument (Roche Diagnostics Corporation, Roche Applied Science, Indianapolis, Ind.).

Nucleic acid extracted from tissues, cells, plasma, serum or hair can be amplified using nucleic acid amplification techniques well known in the art. Many of these amplification methods can also be used to detect the presence of genetic variations simply by designing oligonucleotide primers or probes to interact with or hybridize to a particular target sequence in a specific manner. By way of example, but not by way of limitation, these techniques can include the polymerase chain reaction (PCR), reverse transcriptase polymerase chain reaction (RT-PCR), nested PCR, ligase chain reaction. See Abravaya, K., et al, Nucleic Acids Research, 23:675-682, (1995), branched DNA signal amplification, Urdea, M. S., et al, AIDS, 7 (suppl 2):S11-S 14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al, J Virological Methods, 35:273-286, (1991), Invader Technology, or other sequence replication assays or signal amplification assays. These methods of amplification each described briefly below and are well-known in the art.

Some methods employ reverse transcription of RNA to cDNA. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus Thermophilus*. For example, one method, but not the only method, which may be used to convert RNA extracted from plasma or serum to cDNA is the protocol adapted from the Superscript II Preamplification system (Life Technologies, GIBCO BRL, Gaithersburg, Md.; catalog no. 18089-011), as described by Rashtchian, A., PCR Methods Applic, 4:S83-S91, (1994).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay the nucleic acid releasing reagents and the detection reagents should not be potential inhibitors of amplification enzymes if the ultimate detection is to be amplification based. Amplification methods suitable for use with the present methods include, for example, strand displacement amplification, rolling circle amplification, primer extension preamplification, or degenerate oligonucleotide PCR (DOP).

In one embodiment, PCR is used to amplify a target or marker sequence of interest. The person skilled in the art is capable of designing and preparing primers that are appropriate for amplifying a target sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to the person skilled in the art. For example, the length of a short nucleic acid or oligonucleotide can relate to its hybridization specificity or selectivity.

For analyzing SNPs and other variant nucleic acids, it may be appropriate to use oligonucleotides specific for alternative alleles. Such oligonucleotides which detect single nucleotide variations in target sequences may be referred to by such terms as "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al, Nature, 324: 163-166 (1986); Dattagupta, EP235,726; and Saiki, WO 89/11548. In one embodiment, a probe or primer may be designed to hybridize to a segment of target DNA such that the SNP aligns with either the 5' most end or the 3' most end of the probe or primer.

In some embodiments, the amplification may include a labeled primer, thereby allowing detection of the amplification product of that primer. In particular embodiments, the amplification may include a multiplicity of labeled primers; typically, such primers are distinguishably labeled, allowing the simultaneous detection of multiple amplification products.

In one type of PCR-based assay, an allele-specific primer hybridizes to a region on a target nucleic acid molecule that overlaps a SNP position and only primes amplification of an allelic form to which the primer exhibits perfect complementarity (Gibbs, 1989, Nucleic Acid Res., 17:2427-2448). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456).

In a specific embodiment, a primer contains a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In one embodiment, the mismatched nucleotide in the primer is the second from the last nucleotide at the 3'-most position of the primer. In another embodiment, the mismatched nucleotide in the primer is the last nucleotide at the 3'-most position of the primer.

In one embodiment, primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

It will be appreciated that the invention extends to reagents that do not contain (or that are complementary to) a SNP nucleotide identified herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can readily be detected in order to determine which SNP allele is present at the target SNP site. For example, particular ddNTPs are typically used in the primer extension reaction to terminate primer extension once a ddNTP is incorporated into the extension product. Thus, reagents that bind to a nucleic acid molecule in a region adjacent to a SNP site, even though the bound sequences do not necessarily include the SNP site itself, are also encompassed by the invention.

Variant nucleic acids may be amplified prior to detection or may be detected directly during an amplification step (i.e., "real-time" methods). In some embodiments, the target sequence is amplified and the resulting amplicon is detected by electrophoresis. In some embodiments, the specific mutation or variant is detected by sequencing the amplified nucleic acid. In some embodiments, the target sequence is amplified using a labeled primer such that the resulting amplicon is detectably labeled. In some embodiments, the primer is fluorescently labeled.

In one embodiment, detection of a variant nucleic acid, such as a SNP, is performed using the TaqMan® assay, which is also known as the 5' nuclease assay (U.S. Pat. Nos. 5,210,015 and 5,538,848) or Molecular Beacon probe (U.S. Pat. Nos. 5,118,801 and 5,312,728), or other stemless or linear beacon probe (Livak et al, 1995, PCR Method AppL, 4:357-362; Tyagi et al, 1996, Nature Biotechnology, 14:303-308; Nazarenko et al, 1997, Nucl. Acids Res., 25:2516-2521; U.S. Pat. Nos. 5,866,336 and 6,117,635). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the genetic variations of the invention are useful in diagnosis of erythromelalgia, and can be readily incorporated into a kit format. The invention also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

Other methods of probe hybridization detected in real time can be used for detecting amplification of a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in preferred embodiments, amplified fractions are separated on an agarose gel and stained with ethidium bromide by methods known in the art to detect amplified fragments.

Another suitable detection methodology involves the design and use of bipartite primer/probe combinations such as Scorpion™ probes. These probes perform sequence-specific priming and PCR product detection is achieved using a single molecule. Scorpion™ probes comprise a 3' primer with a 5' extended probe tail comprising a hairpin structure which possesses a fluorophore/quencher pair. The probe tail is "protected" from replication in the 5' to 3' direction by the inclusion of hexethlyene glycol (HEG) which blocks the polymerase from replicating the probe. The fluorophore is attached to the 5' end and is quenched by a moiety coupled to the 3' end. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product. Such probes are described in Whitcombe et al, Nature Biotech 17: 804-807 (1999). Determining Prognosis According to a further aspect of the invention there is provided a kit for diagnosing erythromelalgia which comprises instructions to use said kit in accordance with the methods defined herein.

The kits may be prepared for practicing the methods described herein. Typically, the kits include at least one component or a packaged combination of components useful for practicing the method of the invention. The kits may include some or all of the components necessary to practice method of the invention. Typically, the kits include at least one probe specific for the one or more regions defined herein in at least one container. These components may include, inter alia, nucleic acid probes, nucleic acid primers for amplification of the one or more regions defined herein, buffers, instructions for use, and the like.

It will be appreciated that once an individual has been identified as likely to suffer from or suffering from erythromelalgia, said individual will then be prescribed suitable treatment, such as (5R)-5-(4-{[(2-fluorophenyl)methyl]

oxy}phenyl)-L-prolinamide or a pharmaceutically acceptable salt, solvate or prodrug thereof.

Thus, according to a further aspect of the invention, there is provided a method of treating erythromelalgia in a human subject wherein said method comprises:
(a) detecting the presence of one or more genetic variations within the CACNA1A gene and/or the CACNA1B gene of said subject; and
(b) administering (5R)-5-(4-{[(2-fluorophenyl)methyl]oxy}phenyl)-L-prolinamide or a pharmaceutically acceptable salt, solvate or prodrug thereof to said patient identified as having said one or more genetic variations.

As discussed hereinbefore, current treatment for erythromelalgia is associated with poor tolerability and results in sub-optimal pain control. There is therefore a great need to identify individuals most likely to respond to such therapy.

Thus, according to a further aspect of the invention, there is provided a method of predicting whether an erythromelalgia patient will respond to treatment with (5R)-5-(4-{[(2-fluorophenyl)methyl]oxy}phenyl)-L-prolinamide or a pharmaceutically acceptable salt, solvate or prodrug thereof, wherein said method comprises the steps of:
(a) obtaining a biological sample from a patient; and
(b) detecting the presence of one or more genetic variations within the CACNA1A gene and/or the CACNA1B gene of said subject;
such that the presence of said one or more genetic variations is indicative that an erythromelalgia patient will respond to treatment with (5R)-5-(4-{[(2-fluorophenyl)methyl]oxy}phenyl)-L-prolinamide or a pharmaceutically acceptable salt, solvate or prodrug thereof.

It will be appreciated that once a "responder" has been identified, the patient will then suitably be administered with (5R)-5-(4-{[(2-fluorophenyl)methyl]oxy}phenyl)-L-prolinamide or a pharmaceutically acceptable salt, solvate or prodrug thereof.

Thus, in one embodiment, the method additionally comprises:
(c) administering (5R)-5-(4-{[(2-fluorophenyl)methyl]oxy}phenyl)-L-prolinamide or a pharmaceutically acceptable salt, solvate or prodrug thereof to said erythromelalgia patient identified as having said one or more genetic variations.

According to a further aspect of the invention, there is provided (5R)-5-(4-{[(2-fluorophenyl)methyl]oxy}phenyl)-L-prolinamide or a pharmaceutically acceptable salt, solvate or prodrug thereof for use in the treatment of erythromelalgia in a patient, characterised in that said patient has been selected for having one or more genetic variations within the CACNA1A gene and/or the CACNA1B gene.

According to a further aspect of the invention, there is provided a method of treating erythromelalgia in a patient wherein said method comprises the steps of selecting a patient having one or more genetic variations within the CACNA1A gene and/or the CACNA1B gene followed by administering a therapeutically effective amount of (5R)-5-(4-{[(2-fluorophenyl)methyl]oxy}phenyl)-L-prolinamide or a pharmaceutically acceptable salt, solvate or prodrug thereof to said patient.

Throughout the specification and claims which follow, unless the context requires otherwise, the word 'comprise', and variations such as 'comprises' and 'comprising' will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

EXAMPLES

The invention is illustrated by the Examples described below:

Example 1: (5R)-5-(4-{[(2-Fluorophenyl)methyl]oxy}phenyl)-L-prolinamide (E1)

The compound of Example 1 may be prepared as described in Example 1, Procedures 1 and 2 of WO 2007/042239.

Example 2: (5R)-5-(4-{[(2-Fluorophenyl)methyl]oxy}phenyl)-L-prolinamide Hydrochloride (E2)

The compound of Example 2 may be prepared as described in Example 2, Procedures 1 to 5 of WO 2007/042239.

Example 3: (5R)-5-(4-{[(2-Fluorophenyl)methyl]oxy}phenyl)-L-prolinamide Methanesulfonate (E3)

The compound of Example 3 may be prepared as described in Example 6 of WO 2007/042239.

The following study illustrates the invention:

Whole cell patch-clamp electrophysiology was used to investigate the effects of the compound of Example 2 on human recombinant WT (TTX-R version, Y362S) and 4 mutated Nav1.7 channels from erythromelalgia patients (V400M, I234T, F1449V and S241T), stably expressed in HEK293 cells. Cell reagents were kindly provided by Prof. Stephen Waxman's lab, Yale.

Low frequency (0.1 Hz) stimulation (20 ms test pulse to 0 mV) from two different holding potentials (Vhold) was used to assess the voltage-dependent block by Example 2 and carbamazepine (CBZ). Firstly, Vhold=−90 mV, where most of the channels are in the resting state and secondly Vhold=−60 mV (for V400M and I234T) or Vhold=−70 mV (for F1449V and S241T), which are a physiologically relevant neuronal resting potential. The following solutions were used: External (mM): 140NaCl, 3KCl, 1MgCl$_2$, 1CaCl$_2$, 10 Glucose and 20 HEPES, pH7.3, 320 mOsm; Internal (mM): 140CsF, 10 NaCl, 10 HEPES, 1EGTA, pH 7.3, 310 mOsm. A Hill fit $[Y=(V_{max}*X^{nH})/(IC50^{nH}+X^{nH})]$ on the data was used to determine the IC$_{50}$ and the Hill Coefficient (nH).

Figure 1:
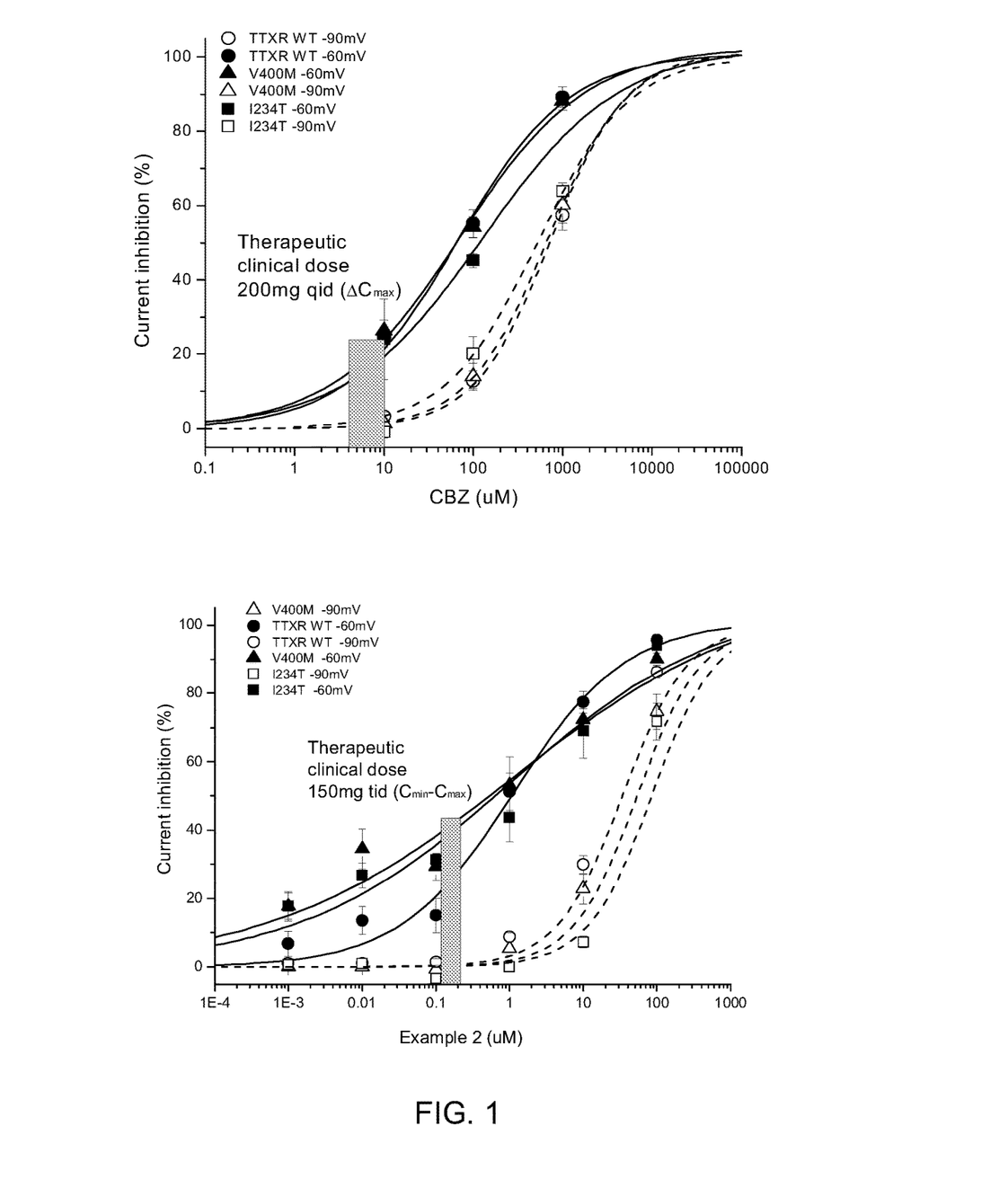
FIG. 1: Whole cell patch-clamp electrophysiology analysis of the compound of Example 2 on human recombinant WT (TTX-R version, Y362S) and 4 mutated Nav1.7 channels from erythromelalgia patients (V400M, I234T, F1449V and S241T), stably expressed in HEK293 cells.

Example 2 blocked the WT, V400M, I234T, F1449V and S241T currents in a voltage-dependent fashion (see FIG. 1). pIC$_{50}$ (the negative log of the IC$_{50}$ concentration) and nH values are summarised in Table 1 and 2 below:

TABLE 1

| | WT pIC$_{50}$ (nH) | V400M pIC$_{50}$ (nH) | I234T pIC$_{50}$ (nH) |
|---|---|---|---|
| Example 2 (Vhold = −90 mV) | 4.5 (1) | 4.3 (1) | 4.1 (1) |
| Example 2 (Vhold = −60 mV) | 6 (0.6) | 6 (0.3) | 6 (0.3) |
| CBZ (Vhold = −90 mV) | 3 (1) | 3.2 (1) | 3.3 (0.8) |
| CBZ (Vhold = −60 mV) | 4.2 (0.7) | 4.2 (0.6) | 3.9 (0.6) |

TABLE 2

| | WT pIC$_{50}$ (nH) | F1449V pIC$_{50}$ (nH) | S241T pIC$_{50}$ (nH) |
|---|---|---|---|
| Example 2 (Vhold = −90 mV) | 4.5 (1) | 4.4 (0.9) | 5.1 (0.8) |
| Example 2 (Vhold = −70 mV) | 5.3 (0.7) | 5.7 (0.4) | 6.4 (0.3) |

Example 2 has demonstrated efficacy in trigeminal neuralgia at 150 mg three times a day, the corresponding free (non protein bound) concentrations are 0.11 and 0.21 µM for Cmin and Cmax respectively. Used at 200 mg four times a day, the range of Cmax free concentrations for CBZ is 4-10 µM. When the free clinical concentration of Example 2 and CBZ are reported on the respective concentration response plots, the level of inhibition of the channel in this particular assay can be measured (see Table 3 and 4):

TABLE 3

| Vhold = −60 mV | WT | V400M | I234T |
|---|---|---|---|
| CBZ | 13-21 | 14-22 | 12-19 |
| Example 2 | 20-28 | 38-42 | 37-42 |

TABLE 4

| (Vhold = −70 mV) | WT | F1449V | S241T |
|---|---|---|---|
| Example 2 | 5-9 | 21-28 | 44-49 |

At free clinical therapeutic concentration, Example 2 is more potent than CBZ in the mutant channels compared to wild type, suggesting that Example 2 differentiates from CBZ and will have specific utility for the treatment of EM patients.

What is claimed is:

1. A method of treating erythromelalgia in a human subject wherein said method comprises:
   (a) detecting the presence of one or more genetic variations within the CACNA1A gene and/or the CACNA1B gene of said subject; and
   (b) administering (5R)-5-(4-{[(2-fluorophenyl)methyl]oxy}phenyl)-L-prolinamide or a pharmaceutically acceptable salt thereof to said patient identified as having said one or more genetic variations.

2. The method according to claim 1, wherein said erythromelalgia is primary erythromelalgia.

3. The method according to claim 1, wherein said erythromelalgia is secondary erythromelalgia.

4. A method of treating Erythromelalgia in a human subject, wherein said method comprises the steps of:
   (a) obtaining a biological sample from a patient;
   (b) detecting the presence of one or more genetic variations within the CACNA1A gene and/or the CACNA1B gene of said subject, such that the presence of said one or more genetic variations is indicative that an erythromelalgia patient will respond to treatment with (5R)-5-(4-{[(2-fluorophenyl)methyl]oxy}phenyl)-L-prolinamide or a pharmaceutically acceptable salt thereof; and
   (c) administering (5R)-5-(4-{[(2-fluorophenyl)methyl]oxy}phenyl)-L-prolinamide or a pharmaceutically acceptable salt thereof to said erythromelalgia patient identified as having said one or more genetic variations.

5. The method according to claim 4, wherein said erythromelalgia is primary erythromelalgia.

6. The method according to claim 4, wherein said erythromelalgia is secondary erythromelalgia.

7. A method of treating erythromelalgia in a patient wherein said method comprises the steps of selecting a patient having one or more genetic variations within the CACNA1A gene and/or the CACNA1B gene followed by administering a therapeutically effective amount of (5R)-5-(4-{[(2-fluorophenyl)methyl]oxy}phenyl)-L-prolinamide or a pharmaceutically acceptable salt thereof to said patient.

8. The method according to claim 7, wherein said erythromelalgia is primary erythromelalgia.

9. The method according to claim 7, wherein said erythromelalgia is secondary erythromelalgia.

* * * * *